United States Patent [19]
Napolitano et al.

[11] Patent Number: 6,106,465
[45] Date of Patent: Aug. 22, 2000

[54] ULTRASONIC METHOD AND SYSTEM FOR BOUNDARY DETECTION OF AN OBJECT OF INTEREST IN AN ULTRASOUND IMAGE

[75] Inventors: David J. Napolitano, Menlo Park; John S. Wang, Sunnyvale, both of Calif.

[73] Assignee: Acuson Corporation, Mountain View, Calif.

[21] Appl. No.: 08/916,854

[22] Filed: Aug. 22, 1997

[51] Int. Cl.$^7$ .................................................. A61B 08/00
[52] U.S. Cl. ........................................................ 600/443
[58] Field of Search ................................. 600/444, 459, 600/443, 447, 458, 448, 437

[56] References Cited

U.S. PATENT DOCUMENTS

| | | |
|---|---|---|
| 3,640,271 | 2/1972 | Horton . |
| 4,712,037 | 12/1987 | Verbeek et al. . |
| 5,111,823 | 5/1992 | Cohen . |
| 5,115,809 | 5/1992 | Saitoh et al. . |
| 5,135,000 | 8/1992 | Akselrod et al. . |
| 5,195,520 | 3/1993 | Schlief et al. . |
| 5,197,477 | 3/1993 | Peterson et al. . |
| 5,233,994 | 8/1993 | Shmulewitz . |
| 5,255,683 | 10/1993 | Monaghan . |
| 5,287,753 | 2/1994 | Routh et al. . |
| 5,313,948 | 5/1994 | Murashita et al. . |
| 5,358,466 | 10/1994 | Aida et al. . |
| 5,386,830 | 2/1995 | Powers et al. . |
| 5,396,285 | 3/1995 | Hedberg et al. . |
| 5,409,688 | 4/1995 | Quay . |
| 5,410,205 | 4/1995 | Gururaja . |
| 5,410,516 | 4/1995 | Uhlendorf et al. . |
| 5,417,213 | 5/1995 | Prince . |
| 5,417,214 | 5/1995 | Roberts et al. . |
| 5,425,366 | 6/1995 | Reinhardt et al. . |

(List continued on next page.)

FOREIGN PATENT DOCUMENTS 0 357 164   of 0000   European Pat. Off. .
0 770 352 A1   5/1997   European Pat. Off. .

OTHER PUBLICATIONS

B. Schrope, et al., "Simulated Capillary Blood Flow Measurement Using A Nonlinear Ultrasonic Contrast Agent," Ultrasonic Imaging 14 (1992).

Chandra M. Sehgal, PhD., et al. "Sonographic Enhancement of Renal Cortex by Contrast Media." J. Ultrasound Med, 14; pp. 741–748 (1995).

Chandra M. Sehgal, PhD., et al., "Influence of Postprocessing Curves on Contrast–Echographic Imaging: Preliminary Studies" J. Ultrasound Med, 14; pp. 735–740 (1995).

Chiang C. Mei, et al., "Parametric resonance of a spherical bubble." J. Fluid Mech. (1991) vol. 229.

Deborah J. Rubens, M.D., "Sonoelasticity Imaging of Prostate Cancer: In Vitro Results." Radiology, vol. 195, No. 2, 1995.

(List continued on next page.)

*Primary Examiner*—Marvin M. Lateef
*Assistant Examiner*—Maulin Patel
*Attorney, Agent, or Firm*—Brinks Hofer Gilson & Lione

[57] ABSTRACT

An ultrasonic method and system for boundary detection of an object of interest in an ultrasound image is provided. One ultrasound imaging system that is provided acquires an ultrasound image from a subject using harmonic information and automatically generates a boundary oriented with respect to an object of interest in the ultrasound image. Another ultrasound imaging system that is provided receives a plurality of user-proposed transition positions oriented with respect to an object of interest in an ultrasound image and automatically generates a computed boundary oriented with respect to the object of interest at least partially as a function of the plurality of user-proposed transition positions. The ultrasound image used in this system can be generated with received ultrasonic energy at a fundamental frequency or at a harmonic of the fundamental frequency.

51 Claims, 5 Drawing Sheets

U.S. PATENT DOCUMENTS

| | | |
|---|---|---|
| 5,433,204 | 7/1995 | Olson . |
| 5,433,207 | 7/1995 | Pretlow, III . |
| 5,438,554 | 8/1995 | Seyed-Bolorforosh et al. . |
| 5,443,071 | 8/1995 | Banjanin et al. . |
| 5,456,255 | 10/1995 | Abe et al. . |
| 5,456,257 | 10/1995 | Johnson et al. . |
| 5,457,754 | 10/1995 | Han et al. . |
| 5,469,849 | 11/1995 | Sasaki et al. . |
| 5,471,990 | 12/1995 | Thirsk . |
| 5,479,926 | 1/1996 | Ustuner et al. . |
| 5,482,046 | 1/1996 | Deitrich . |
| 5,526,816 | 6/1996 | Arditi . |
| 5,538,003 | 7/1996 | Gadonniex et al. . |
| 5,540,909 | 7/1996 | Schutt . |
| 5,558,092 | 9/1996 | Unger et al. . |
| 5,560,364 | 10/1996 | Porter . |
| 5,577,505 | 11/1996 | Brock-Fisher et al. . |
| 5,579,768 | 12/1996 | Klesenski . |
| 5,579,770 | 12/1996 | Finger . |
| 5,588,435 | 12/1996 | Weng et al. . |
| 5,601,085 | 2/1997 | Ostensen et al. . |
| 5,601,086 | 2/1997 | Pretlow, III et al. . |
| 5,608,690 | 3/1997 | Hossack et al. . |
| 5,617,862 | 4/1997 | Cole et al. . |
| 5,628,322 | 5/1997 | Mine . |
| 5,632,277 | 5/1997 | Chapman et al. . |
| 5,879,303 | 3/1999 | Averkiou et al. . |

OTHER PUBLICATIONS

Eric J. Chen, et al., "Young's Modulus Measurements of Soft Tissues with Application to Elasticity Imaging." IEEE Transactions on Ultrasonics, Ferroelectrics, and Frequency Control, vol. 43, No. 1, Jan. 1996.

Fred Lee, Jr., M.D., "Sonoelasticity Imaging: Results in in Vitro TIssue Specimens." Radiology, vol. 181, No. 1 Oct. 1991.

H. Edward Karrer, et al., "A Phased Array Acoustic Imaging System for Medical Use." 1980 Ultrasonics Symposium.

"HP Ultrasound Technologies—Viability." About HP Ultrasound Imaging, WWW document 1997.

J. Ophir, et al., "Elastography: A Quantitative Method for Imaging the Elasticity of Biological Tissues." Ultrasonic Imaging 13, (1991).

J. W. Norris, "The non–linear oscillation of a radially symmetric bubble in a time periodic pressure field." Dynamics and Stability of Systems, vol. 9, No. 1 (1994).

J.A. Hossack, et al., "Improving transducer performance using multiple active layers." SPIE vol. 1733 (1992).

Janet B. Jones–Oliveira, et al., "Transient fluid—solid interaction of submerged spherical shells revisited: Proliferation of frequencies and acoustic radiation effects." Acoustical Society of America, 96(2) Pt. 1, Aug. 1994.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

K.J. Parker, et al., "Tissue Response to Mechanical Vibrations for 'Sonoelasticity Imaging'." Ultrasound in Med. & Biol., vol. 16, No. 3, (1990).

Ken Ishihara et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

Kevin J. Parker, PhD, et al., "Sonoelasticity of Organs: Shear Waves Ring a Bell." J. Ultrasound Med. 11 (1992).

Kotaro Sato, et al., "Numerical analysis of a gas bubble near a rigid boundary in an oscillatory pressure field." J. Acoustical Society of America, 95 (5), May 1994.

L.W. Anson et al., "Ultrasonic scattering from spherical shells including viscous and thermal effects." J. Acoustical Society of America, 93 (4), Apr. 1993.

Marc Gensane, "Bubble population measurements with a parametric array." 1994 Acoustical Society of America, 95 (6) Jun.

Michael S. Longuet–Higgins, Resonance in nonlinear bubble oscillations. J. Fluid Mech. (1991) vol. 224.

Michalakis A. Averkiou, et al., "Self–demodulation of amplitude–and frequency–modulated pulses in a thermoviscous fluid." J. Acoustical Society of America, 94 (5), Nov. 1993.

Nico de Jong, "Physical properties and technical aspects of ultrasound contrast agents."

Pi Hsien Chang, et al., "Second Harmonic Imaging and Harmonic Doppler Measurements with Albunex." IEEE Transactions on Ultrasonics, Ferroelectrics, and Frequency Control, vol. 42, No. 6, Nov. 1996.

Robert M. Lerner, et al., "'Sonoelasticity' Images Derived from Ultrasound Signals in Mechanically Vibrated Tissues." Ultrasound in Med. and Biol., vol. 16, No. 3, 1990.

Sharon L. Mulvagh, M.D., et al., "Abstract Session IV Contrast and Ischemia." Journal of the American Society of Echocardiography, vol. 8, No. 3, May 1995.

Shmuel Gottlieb, M.D. et al., "Effect of Pressure on Echocardiographic Videodensity from Sonicated Albumin: An In Vitro Model." J. Ultrasound Med. 14 (1995).

"Supplement to Journal of the American College of Cardiology." American College of Cardiology, $45^{th}$ Annual Scientific Session, Mar. 24–27, 1996 pp. 21A, 63A, 239–240A.

T.G. Leighton, "Transient excitation of insonated bubbles." Research Notes.

Ted Christopher, "Finite Amplitude Distortion–Based Inhomogeneous Pulse Echo Ultrasonic Imaging." IEEE Transactions on Ultrasonics, Ferroelectrics, and Frequency Control, vol. 44, No. 1, Jan. 1997.

V.L. Newhouse, et al., "Bubble size measurements using the nonlinear mixing of two frequencies." J. Acoust. Soc. Am. 75 (5), May 1984.

Vokmar Uhlendorf, et al., "Nonlinear Acoustical Response of Coated Microbubbles in Diagnostic Ultrasound." IEEE 1994 Ultrasonics Symposium.

William Armstrong, M.D., et al., "American Society of Echocardiography Position Paper on Contrast Echocardiography."draft 1–Jun. 6, 1994.

Yang–Sub Lee, et al., "Time–domain modeling of pulsed finite–amplitude sound beams." J. Acoustical Society of America, 97 (2), Feb. 1995.

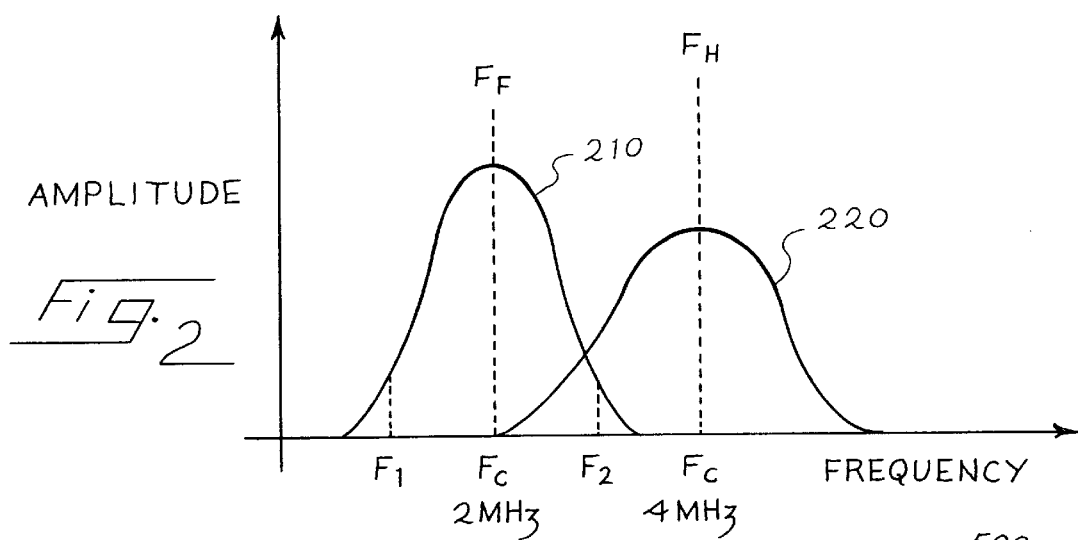
Fig. 2
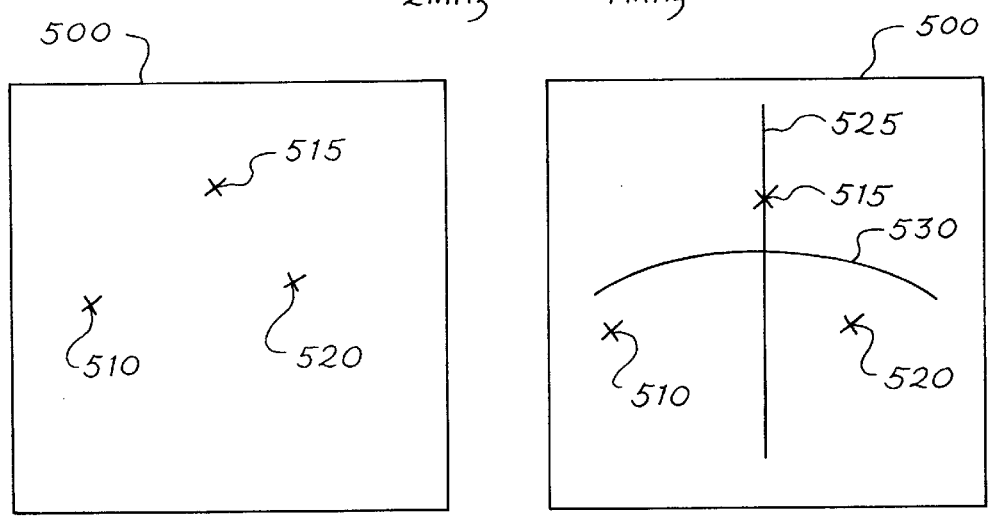
Fig. 5A
Fig. 5B
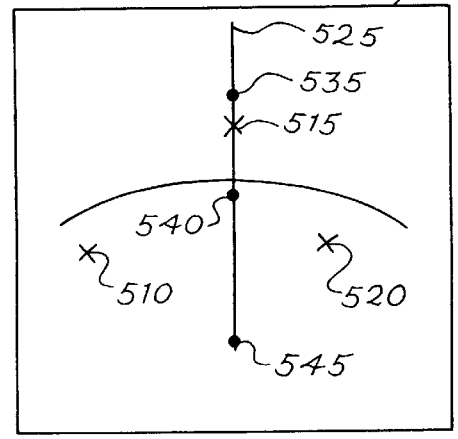
Fig. 5C
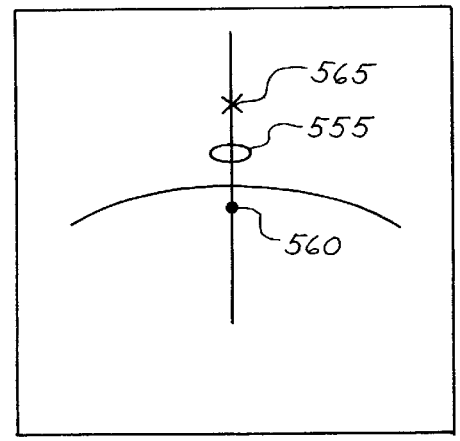
Fig. 5D

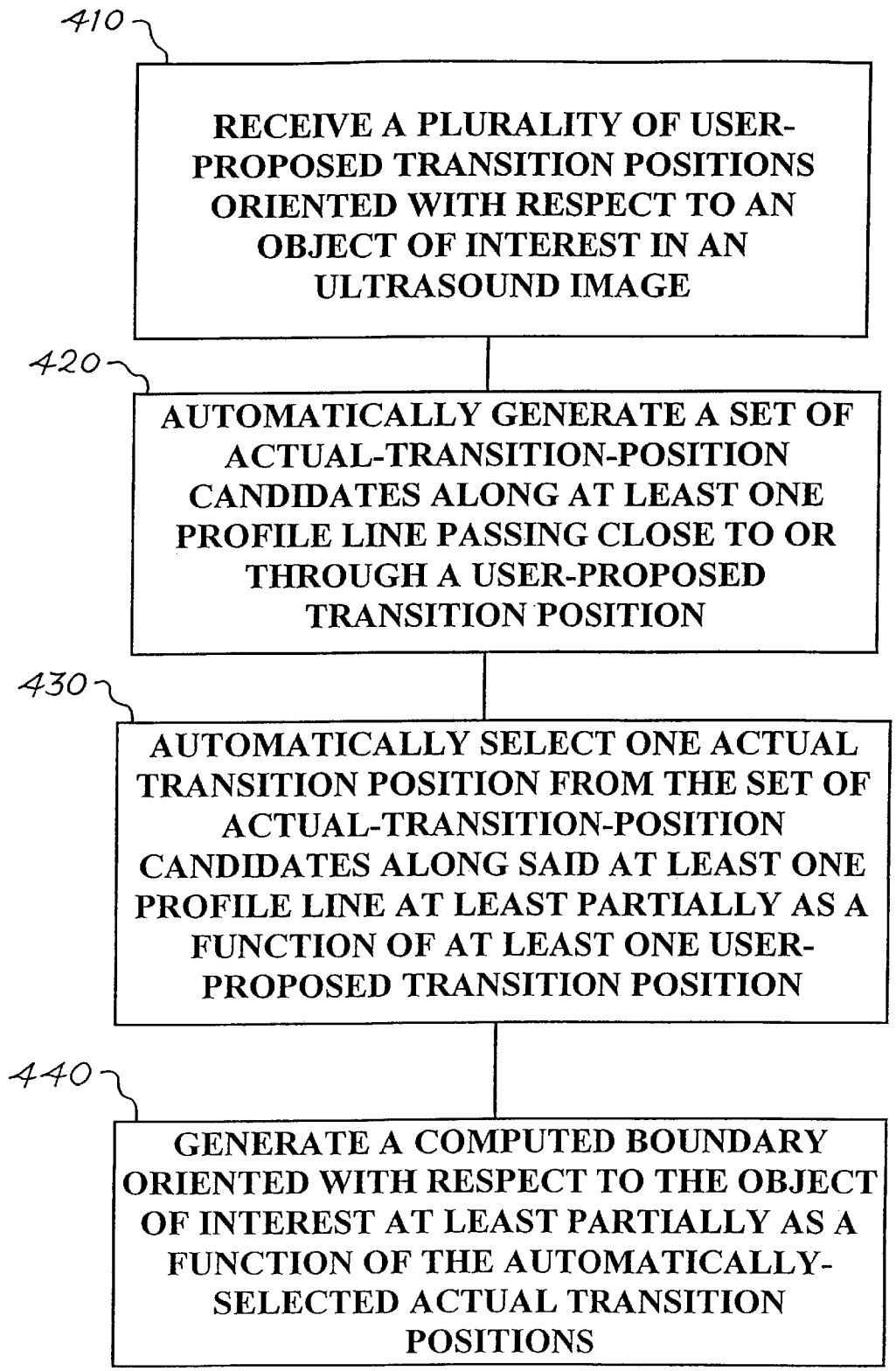

ULTRASONIC METHOD AND SYSTEM FOR BOUNDARY DETECTION OF AN OBJECT OF INTEREST IN AN ULTRASOUND IMAGE

BACKGROUND OF THE INVENTION

In medical ultrasound imaging, it is often desired to generate a boundary around an object of interest in an ultrasound image. For example, if the object of interest is a heart chamber, the area and perimeter of the chamber can be computed from the generated boundary. With this data, quantitative information can be obtained about various cardiac functions, such as cardiac wall motion, pressure-volume ratio, volumetric changes, blood pumping efficiency, and blood pumping volume. As another example, if the object of interest in the ultrasound image is a spectral Doppler strip, the boundary (corresponding to the envelope of the strip) represents the maximum velocity waveform—the highest velocity component in the Doppler spectrum that corresponds to flow.

To generate a boundary, a user employs either automatic or manual boundary-detection techniques. With automatic boundary-detection, various computational techniques can be used to automatically generate a boundary around an object of interest without user intervention. These techniques are well known in the art and generally detect the dividing line between a bright region and a dark region by thresholding ultrasound image data. While automatic boundary-detection techniques can quickly detect a boundary without user intervention, the detected boundary is often unacceptable. For example, a major problem in detecting boundaries in ultrasound images generated with fundamental frequencies is the presence of acoustic clutter. Acoustic clutter is generally associated with degraded beamforming due to body wall aberrations and is often present in obese patients, typically termed "hard-bodies." Acoustic clutter obscures the boundary between bright and dark regions, causing automatic boundary-detection algorithms to compute erroneous borders. Additionally, other forms of noise, such as speckle, can result in the generation of erroneous borders.

When erroneous borders are generated by an automatic boundary detection technique or when an automatic boundary detection technique is not used, a user typically must resort to manual tracing to generate a boundary. With manual boundary detection, the user views the ultrasound image on a display and traces an outline around the entire object of interest using a user interface, such as a track ball, joystick, or mouse. Because the ultrasound system uses the user-drawn boundary to calculate quantitative information, the user must be very precise in drawing the boundary. As a result, manual boundary detection is both a time consuming and taxing process for the user. This process is made even more difficult in ultrasound images generated with fundamental frequencies because acoustic clutter renders the borders difficult to see.

There is, therefore, a need for a method and system for boundary detection of an object of interest in an ultrasound image that will overcome the problems described above.

SUMMARY OF THE INVENTION

The present invention is directed to an ultrasonic method and system for boundary detection of an object of interest in an ultrasound image.

According to a first aspect of this invention, an ultrasound imaging system is provided for acquiring an ultrasound image from a subject using harmonic information and for automatically generating a boundary oriented with respect to an object of interest in the ultrasound image. Using harmonic information generates ultrasound images with significantly better image quality. With better image quality, the automatic boundary detection technique used by the system can generate a more accurate boundary estimate, reducing the need to resort to manual tracing.

An ultrasound image can be generated from a subject using harmonic information by transmitting ultrasonic energy at a fundamental frequency along a plurality of transmit lines and receiving ultrasonic energy at a harmonic, such as a second order harmonic, of the fundamental frequency along a plurality of receive lines formed in response to one of said transmit lines. The subject can be free of non-native non-linear contrast agents throughout an entire imaging session, or a non-linear contrast agent can be provided to the subject during an imaging session.

According to a second aspect of this invention, an ultrasonic imaging system is provided for receiving a plurality of user-proposed transition positions oriented with respect to an object of interest in an ultrasound image for automatically generating a computed boundary oriented with respect to the object of interest at least partially as a function of the plurality of user-proposed transition positions. This system offers a fast and easy alternative to manual tracing of a boundary when, for example, automatic boundary techniques generate erroneous boundaries.

The ultrasound image can be generated with received ultrasonic energy at a fundamental frequency or at a harmonic of the fundamental frequency, such as a second order harmonic. Additionally, the subject can be free of non-native non-linear contrast agents throughout an entire imaging session, or a non-linear contrast agent can be provided to the subject during an imaging session.

The imaging system can perform a method for user-guided detection of a boundary of an object of interest in an ultrasound image comprising the steps of (a) receiving a plurality of user-proposed transition positions oriented with respect to an object of interest in an ultrasound image; (b) automatically generating a set of actual-transition-position candidates along at least one profile line passing close to or through a user-proposed transition position, said step of automatically generating being repeated for a plurality of user-proposed transition positions; (c) automatically selecting one actual transition position from the set of actual-transition-position candidates along said at least one profile line, the automatically selecting being made at least partially as a function of at least one user-proposed transition position of the plurality of user-proposed transition positions, said step of automatically selecting being repeated for a plurality of user-proposed transition positions; and (d) generating a computed boundary oriented with respect to the object of interest, said boundary being oriented at least partially as a function of the actual transition positions automatically selected in step (c).

The preferred embodiments of the invention will now be described with reference to the attached drawings.

BRIEF DESCRIPTION OF THE DRAWINGS

FIG. 2 is a graph displaying two frequency bands representing acquired fundamental and harmonic frequencies and associated amplitudes.

FIG. 4 is a flow chart of a method of user-guided detection of a boundary of an object of interest in an ultrasound image.

FIGS. 5A–5D illustrate a method of user-guided detection of a boundary of an object of interest in an ultrasound image.

FIG. 5A shows a plurality of user-proposed transition positions in an ultrasound image.

FIG. 5B shows a profile line being normal to a tangent of a curve fitting the plurality of user-proposed transition positions.

FIG. 5C illustrates a first, second, and third actual-transition-position candidate along a profile line.

FIG. 5D illustrates a computed position which is a weighed average of an automatically selected actual transition position and a user-proposed transition position.

DETAILED DESCRIPTION OF THE PRESENTLY PREFERRED EMBODIMENTS

Figure 1:
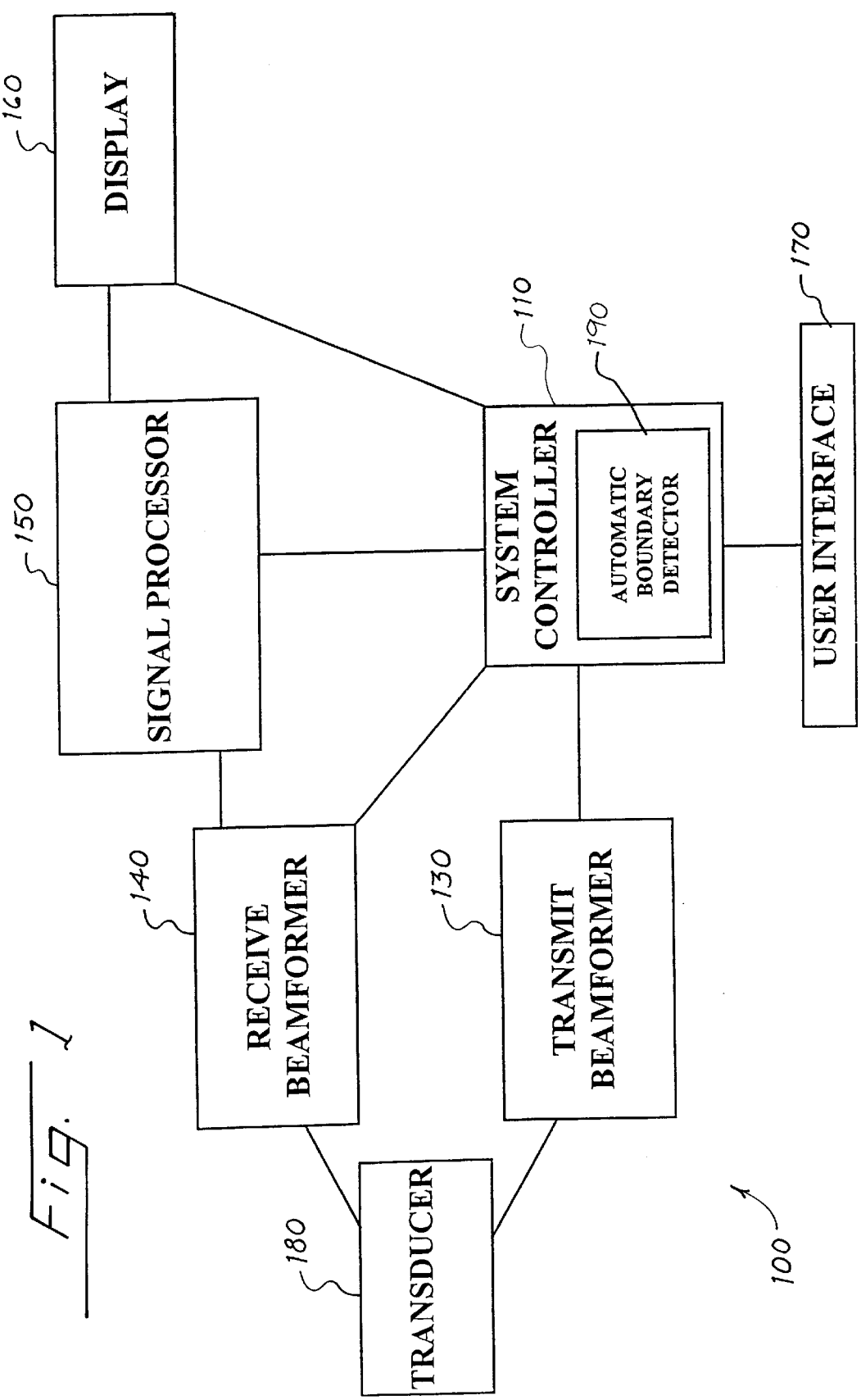
FIG. 1 is a block diagram of an ultrasound imaging system of a first preferred embodiment.

Now turning to the drawings, FIG. 1 is a block diagram of an ultrasound imaging system 100 of a first preferred embodiment. This imaging system 100 is capable of automatically generating a boundary around an object of interest in an ultrasound image generated from harmonics of a fundamental frequency. As shown in this figure, a system controller 110 is coupled to a transmit beamformer 130, a receive beamformer 140, a signal processor 150, and a display 160 and is responsive to a user interface 170. A transducer 180 is responsive to the transmit beamformer 130 and coupled to the receive beamformer 140. As used herein, "coupled to" means directly coupled to or indirectly coupled through one or more components, and "responsive to" means directly responsive to or indirectly responsive through one or more components. The system controller 10 of this preferred embodiment contains an automatic boundary detector 190 comprising means for automatically generating a boundary around an object of interest. The components of this system 100 will be described in more detail below.

Using the user interface 170, the user selects the type of ultrasound image or images for display. The user interface 170 can be of any construction known in the art, such as a keyboard, track ball, joystick, touch pad, touch screen, or any combination of such devices. As used herein, the term ultrasound image includes, but is not limited to, a B-mode image, an M-mode image, an F-mode image (e.g., color Doppler velocity image (CDV) or color Doppler energy image (CDE)), a Doppler Tissue image (DTI), a spectral Doppler strip image (e.g., a CW or PW spectral Doppler image), or any combination of these images.

The user also selects a transmit frequency and a receive frequency associated with each image. The frequencies available for selection include at least one receive frequency that is a harmonic of the transmit frequency and at least one receive frequency that is a fundamental of the transmit frequency, although other combinations may be provided. Harmonic frequencies are frequencies associated with non-linear propagation or scattering of transmit signals. As used herein, harmonic includes subharmonics as well as second, third, fourth, and other harmonics. Fundamental frequencies are frequencies corresponding to linear propagation and scattering of transmit signals. Non-linear propagation or scattering corresponds to shifting energy associated with a frequency or frequencies to another frequency or frequencies. The selected frequencies associated with each image are preferably within the frequency range of the transducer 180. Based on input from the user interface 170, the system controller 110 provides control instructions to the transmit beamformer 130, the receive beamformer 140 (to generate, for example, the appropriate in phase and quadrature (I and Q) information), and the signal processor 150. As is described in more detail below, the system 100 transmits ultrasonic energy at a fundamental frequency along a plurality of transmit lines and receives ultrasonic energy at a harmonic of the fundamental frequency along a plurality of receive lines formed in response to one of said transmit lines.

Based on the various user selections, the transmit beamformer 130 is configured. The transmit beamformer 130 is of a construction known in the art, such as a digital—or analog-based beamformer capable of generating signals at different frequencies. The transmit beamformer 130 generates one or more excitation signals. Each excitation signal has an associated center frequency. As used herein, the center frequency represents the frequency in a band of frequencies approximately corresponding to the center of the amplitude distribution.

FIG. 2 shows a graph of fundamental and second order harmonic frequencies and associated amplitudes, wherein a transmit signal with a bandwidth approximately corresponding to frequencies F1 and F2 is transmitted. A first frequency band 210 represents the acquired fundamental frequencies and associated amplitudes. A second frequency band 220 represents acquired frequencies and associated amplitudes corresponding to non-linear propagation or scattering. For example, the second frequency band 220 corresponds to the second order harmonic frequencies of the transmitted signal. As shown in FIG. 2, some of the fundamental frequencies may also include harmonic frequency information and vice versa, that is, more or less overlap may occur.

Since the amplitude distribution is Gaussian, the center frequency, $F_c$, is half of the sum of frequencies F1 and F2 in the first band 210. Other amplitude distributions with different center frequencies may be used. The center frequency associated with each excitation signal is substantially the same as the selected transmit frequency. Preferably, the center frequency of the excitation signals is within the 1 to 15 MHz, range, such as 2 MHz, and accounts for the frequency response of the transducer 180. Except for CW spectral Doppler, the excitation signals preferably have non-zero bandwidth, such as represented by the first 210 or second 220 bands.

Referring again to FIG. 1, the excitation signals from the transmit beamformer 130 are provided for the transducer 180. The transducer 180 is of any construction known in the art, such as a multiple-element piezoelectric transducer. One or more of the elements in the transducer 180 are excited by an excitation signal to produce ultrasonic waveforms. As known in the art, the waveforms are focused along ultrasonic beams or lines in one of various formats, such as steered linear, sector, or Vector®. The ultrasonic waves are focused using various delay and apodization techniques. The ultrasonic waves have a center frequency, such as 2 MHz, and a bandwidth associated with the frequency of the excitation signals. Thus, the center frequency of the ultrasonic waves corresponds to one of the transmit frequencies selected by the user.

The focused ultrasonic waves propagate through a body and reflect off various structures, such as blood cells and tissue, both linearly and non-linearly. Some of the reflected waves return as echo signals to the transducer 180. The echo signals excite the elements of the transducer 180. The elements generate voltage signals corresponding to the echo signals. These voltage signals are provided to the receive beamformer 140.

The receive beamformer 140 is of a construction known in the art, such as an analog or digital receive beamformer capable of processing signals associated with different frequencies. The receive beamformer 140 and the transmit beamformer 130 may comprise a single device. As known in the art, each voltage signal is delayed, apodized, and suimnmed with other voltage signals. An ongoing stream of summed signals represents the ultrasound beam or line received from the body.

The receive beamformer 140 also demodulates the summed signals to baseband. The demodulation frequency is selected in response to the fundamental frequency or another frequency, such as a second order harmonic frequency. Preferably, the receive beamformer 140 is capable of demodulating in response to differing demodulation frequencies, such as fundamental, sub-harmonic, second order harmonic, third order harmonic, or fourth order harmonic frequencies. For example, the transmitted ultrasonic waveforms are transmitted at a 2 MHz center frequency, similar to the first band 210 in FIG. 2. The summed signals are then demodulated to baseband by shifting by either the fundamental 2 MHz or the second order harmonic 4 MHz frequency (the demodulation frequency). Signals associated with frequencies other than near baseband are removed by low-pass filtering. As an alternative or in addition to demodulation, the receive beamformer 140 provides bandpass filtering. Thus, signals associated with frequencies other than a range of frequencies centered around the desired receive minus any demodulation frequency are filtered from the summed signals. The demodulated or filtered signal is passed to the signal processor 150 as a complex I and Q signal, but other types of signals, such as real value signals, may be passed. The I and Q signals referred to herein may be replaced by other types of signals, such as real value signals. From the signal processor 150, the ultrasound image can be presented to the user on the display 160, based on further processing known in the art, such as scan conversion.

As described above, the system controller 110 of this preferred embodiment contains an automatic boundary detector 190 comprising means for automatically generating a boundary around an object of interest. Specifically, the detector 190 contains means for retrieving ultrasound image data associated with spatial locations in the ultrasound image and means for processing ultrasound image data of a plurality of spatial locations to detect a boundary. Ultrasound image data includes, but is not limited to, pixel intensity values corresponding to processed echo signals, raster scan data, data following detection in a B-mode processing chain, data following parameter estimation in a Color Doppler chain, and data following computation of the discrete Fourier transform in Doppler processing.

Automatic boundary detection software running on a microprocessor in the detector 190 can retrieve and process ultrasound-image data from an image-data buffer in the detector 190 to generate a boundary. It is important to note that one or more functions described herein as being performed by the detector 190 can be performed in other components of the system 100. Additionally, the detector 190 can reside in a component separate from those shown in FIG. 1.

Automatic boundary detection using ultrasound image data associated with spatial locations in the ultrasound image is well known in the art. A preferred automatic boundary-detection technique uses a selected threshold cut-off to detect a boundary. The threshold cut-off may vary due to operator input and the structure represented in the ultrasound image. For example, if the ultrasound image is a B-mode image, echo signals used to derive B-mode intensity values are obtained for a plurality of spatial locations in the ultrasound image and passed through a spatial or temporal low-pass filter to smooth the echo signals for reliability. The threshold cut-off is then applied to the corresponding B-mode pixel intensity values (i.e., the ultrasound image data). Preferably, the threshold cut-off is selected to define B-mode intensities associated with structure from B-mode intensities not associated with structure. The pixels corresponding to structure surrounding pixels corresponding to no structure define the boundary.

This method can be also used with other imaging modes. For example, if the ultrasound image is an F-mode image, the threshold cut-off would be applied to Doppler velocity values instead of B-mode pixel intensity values in a plurality of spatial locations in the ultrasound image. The threshold cut-off would define a velocity value separating velocity values corresponding to tissue motion from velocity values corresponding to fluid or blood motion. The boundary would be defined by spatial locations with corresponding velocity values above the cut-off.

It is preferred that the automatic boundary detection technique be performed on ultrasound images non-linearly generated using second harmonic frequencies. Second harmonic frequencies produce ultrasound images with dramatically reduced acoustic clutter and better beamforming than the fundamental image counterpart. Because of the significantly better image quality, the automatic boundary detection technique can generate a more accurate boundary estimate, reducing the need to resort to manual tracing even under hard body conditions. That is, the detected border is easier to obtain with a second-harmonic image than with a fundamental image.

In addition to the technique described above, other automatic boundary detection techniques can be used. U.S. Pat. No. 5,538,003 to Gadonniex et al., for example, describes three other automatic boundary-detection techniques for processing ultrasound image data in spatial locations throughout an ultrasound image, One technique discussed in Gadonniex et al. determines whether the reflections of a transmitted pulse are from tissue or blood. A boundary is detected where a majority of the signals for both a current scan line and at least one previous scan line indicate similar reflections. Another technique uses a (gain control circuit along one or more scan lines to maintain a substantially constant gain level. A boundary is detected based upon a discrimination in levels between return pulses, with tissue generally returning a higher level signal than blood. A third technique illustrated in Gadonniex et al. determines pixel changes from tissue-to-blood or blood-to-tissue over succeeding display frames, and pixels evidencing like change are assigned a common appearance. When succeeding frames are compared, a boundary is indicated by a binary change in pixel appearance from one frame.

U.S. Pat. No. 5,457,754 to Han et al. discusses another automatic boundary-detection technique. As described in Han et al., a boundary of an object of interest is detected by analyzing the radial distance to an object boundary along radial lines emanating from the center of the object. It is important to note that the automatic boundary-detection techniques described above are merely examples and that other techniques can be used.

Figure 3:
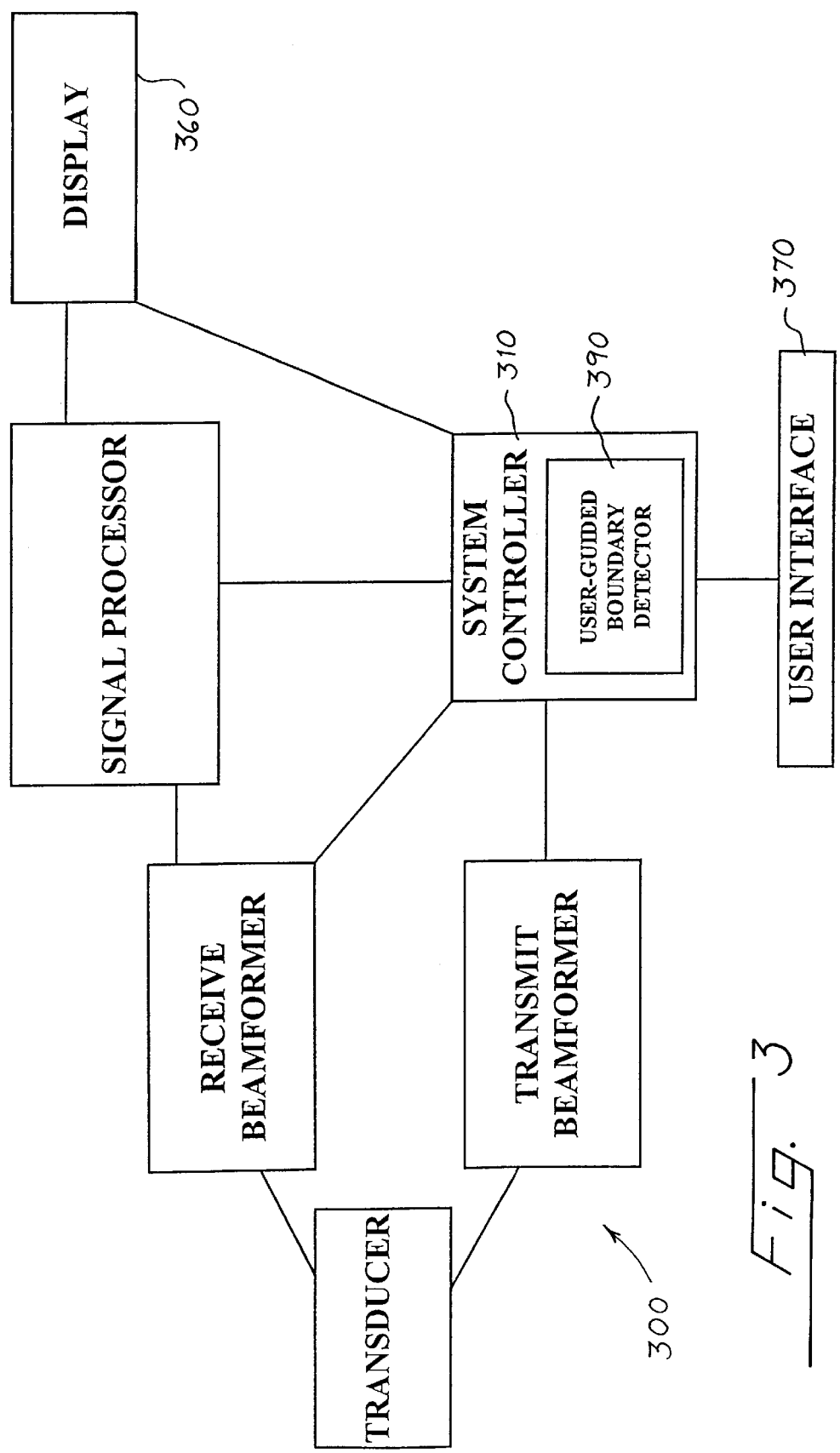
FIG. 3 is a block diagram of an ultrasound imaging system of another preferred embodiment.

Turning again to the drawings, FIG. 3 shows a block diagram of an ultrasound imaging system 300 of another preferred embodiment. This imaging system 300 is capable of performing user-guided boundary detection of an object of interest in an ultrasound image. This system 300 contains similar components as that of the system 100 of the first preferred embodiment and, like that system 100, can generate ultrasound images at fundamental frequencies, harmonic frequencies, or a combination of fundamental frequencies and harmonic frequencies.

Unlike the system 100 of the first preferred embodiment, the system controller 310 of this system 300 contains a user-guided boundary detector 390. As described in more detail below, the detector 390 comprises means for user-guided boundary detection. Such means can be implemented using software running on a microprocessor in the detector 390, although a hardware implementation can be used. A preferred method of implementing user-guided boundary detection is listed in the software code below, which can be executed on Matlab software. For real time operation in an ultrasound system, it is preferred that this code be implemented in C or another suitable language. It is also important to note that one or more functions described herein as being performed by the detector 390 can be performed in other components of the system 300. Additionally, the detector 390 can reside in a component separate from those shown in FIG. 3.

Generally, the user-guided boundary detector 390 receives, from the user interface 370, a plurality of user-proposed transition positions oriented with respect to an object of interest in an ultrasound image and automatically generates a computed boundary oriented with respect to the object of interest. The computed boundary is positioned at least partially as a function of at least one user-proposed transition position. A "user-proposed transition position" is a location in the ultrasound image that the user selects as being near or on the boundary of the object of interest.

Specifically, the user-guided boundary detector 390 implements a method for user-guided detection of a boundary of an object of interest in an ultrasound image. FIG. 4 is a flow chart illustrating the steps of this method. As illustrated in FIG. 4, the detector 390 first receives a plurality of user-proposed transition positions oriented with respect to an object of interest in an ultrasound image (step 410). Next, the detector 390 automatically generates a set of actual-transition-position candidates along at least one profile line passing close to or through a user-proposed transition position (step 420). The detector 390 then automatically selects one actual transition position from the set of actual-transition-position candidates along said at least one profile line at least partially as a function of at least one user-proposed transition position (step 430). Steps 420 and 430 can be repeated for a plurality of user-proposed transition positions. Then, the detector 390 generates a computed boundary oriented with respect to the object of interest at least partially as a function of the automatically-selected actual transition positions (step 440). The steps of this method will be described in more detail below and with reference to FIGS. 5A–5D.

The first step shown in FIG. 4 is receiving a plurality of user-proposed transition positions oriented with respect to an object of interest in an ultrasound image (step 410). After seeing the ultrasound image presented on the display 360, the user can manipulate the user interface 370 to control a cursor position on the display 360. In this way, the user can quickly place a plurality of user-proposed transition positions along an object of interest in the ultrasound image. For example, the user can use a track ball to position a cursor along the object of interest image and press a select button to register the position of the cursor with the detector 390 as a user-proposed transition position. Alternatively, user-proposed transition positions can be sampled from a line drawn by a user, for example, with a mouse or stylus. FIGS. 5A shows a plurality of user-proposed transition positions 510, 515, 520 in an ultrasound image 500.

After receiving the user-proposed transition positions, a set of actual-transition-position candidates along at least one profile line passing close to or through a user-proposed transition position is automatically generated (step 420). As used herein, "set" includes one or more than one element, and "profile line" refers to a sequence of spatial locations in the ultrasound image comprising ultrasound image data. While profile lines can be formed in any direction with respect to user-selected transition positions, it is preferred that the profile lines be lines normal to a tangent to a curve fitting the plurality of user-proposed transition positions. FIG. 5B shows a profile line 525 normal to a tangent of a curve 530 fitting the plurality of user-proposed transition positions 510, 515, 520. Alternatively, the curve can connect the plurality of user-proposed transition positions, such as when user-proposed transition positions are sampled from a line drawn by a user.

To generate the set of actual-transition-position candidates, image data along the profile line is retrieved, for example, from a buffer in the detector 390. The retrieved image data is then processed by a suitable edge detection algorithm to generate the set of actual-transition-position candidates along the profile line. An actual-transition-position candidate is a location along the profile line having an ultrasound image data value characteristic of a boundary.

For example, if ultrasound image data represents pixel intensity values in a scan-converted B-mode image, differences in pixel intensity values between adjacent locations along the profile line can be identified. Actual-transition-position candidates can be adjacent pixel locations along the profile line having a difference above a threshold level. These locations indicate boundaries between light and Clark regions. As another example, along a spectral line in a spectral Doppler strip, an actual-transition-position candidate is a location farthest away from a baseline or DC value having the highest pixel intensity which exceeds a threshold. Other edge detection techniques can be used including, but not limited to, calculating where a derivative of a profile line is a maximum and calculating where an absolute value of an integral of a profile line reaches a maximum. To reduce the computation requirements, a filtering operation, such as a low-pass filter, can be applied to the profile line in order to reduce the number of identified transitions which are probably not of interest to the user. FIG. 5C shows a first 535, a second 540, and a third 545 actual-transition-position candidate along the profile line 525.

After the set of actual-transition-position candidates is generated, the detector 390 automatically selects one actual transition position from the set of actual-transition-position candidates (step 430). The detector 390 automatically makes the selection at least partially as a function of at least one user-proposed transition position. The selection can be made, for example, by determining which actual-transition-position candidate is closest to the user-proposed transition position along a profile line (the first candidate 535 in FIG. 5C) or closest to a curve fitting the plurality of user-proposed transition positions (the second candidate 540 in FIG. 5C). Additionally, previously automatically selected actual transition positions can be used in the selection process. For example, the chosen candidate can be the one closest to a curve fitting a plurality of previously automatically selected actual transition positions.

The last step in the method of this preferred embodiment is to generate a computed boundary oriented with respect to the object of interest at least partially as a function of the automatically selected actual transition positions (step 440). The boundary can simply be a curve fitting the plurality of actual transition positions. Alternatively, the boundary can be a curve fitting a plurality of computed position locations. A computed position location can be a function of the user-proposed transition positions. For example as FIG. 5D shows, the computed position 555 can be a weighed average of an automatically selected actual transition position 560 and a user-proposed transition position 565. A computed position can also be an average of a plurality of actual transition positions along a plurality of profile lines. The computed position location could even be the user-selected transition position if an actual transition position cannot be identified or if the actual transition position would result in an erroneous boundary (e.g., when the actual transition position is farther away than a threshold distance from a certain location in the ultrasound image such as a user-proposed transition position).

The automatically generated boundary can be presented on the display 360 as the user is drawing the user-drawn boundary (i.e., entering user-proposed transition positions via the user interface 370). In this way, it appears that the automatically-generated boundary is being drawn by the user in real time, even though the boundary displayed on the display 360 may not comprise the user-proposed transition positions.

As mentioned above, the term ultrasound image includes, but is not limited to, a B-mode image, an M-mode image, an F-mode image (e.g., color Doppler velocity image (CDV) or color Doppler energy image (CDE)), a Doppler Tissue image (DTI), a spectral Doppler strip image (e.g., a CW or PW spectral Doppler image), or any combination thereof. If, for example, the ultrasound image comprises a scan-converted B-mode ultrasound image of a heart, the computed boundary can be a boundary of a heart wall (i.e., the object of interest).

Figure 6A:
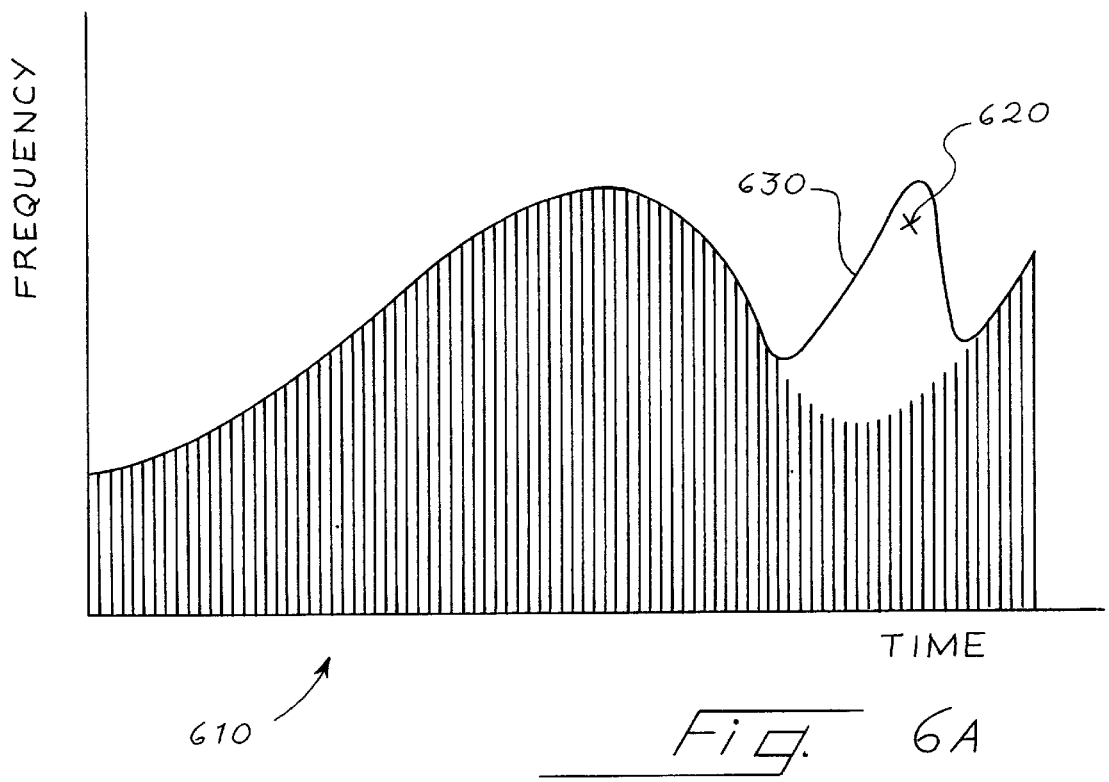
FIG. 6A is a graph of a spectral Doppler strip with an erroneous boundary generated by an automatic boundary detection technique.
Figure 6B:
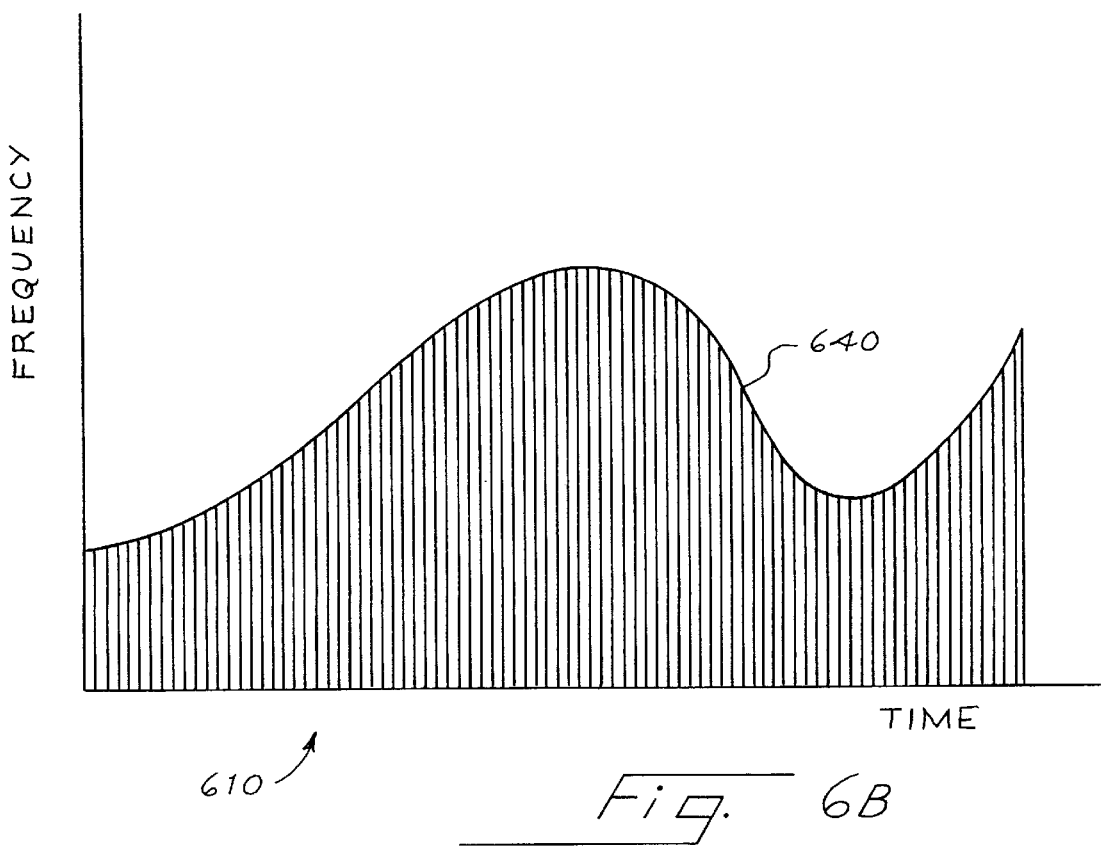
FIG. 6B is a graph of a spectral Doppler strip with a boundary generated with a user-guided boundary detection technique.

As another example the ultrasound image can comprise a spectral Doppler strip, as shown in the graphs 610 of FIGS. 6A and 6B. A spectral strip is a collection of consecutive one-dimensional spectra. These spectra are juxtaposed to form a two-dimensional spectral strip. A computed boundary of the two-dimensional spectral strip (i.e., the object of interest in the ultrasound image) is the envelope of the maximum velocity waveform of the spectral Doppler strip. As FIG. 6A shows, the presence of noise 620 often causes an automatic boundary detection technique to generate an erroneous boundary 630. By using the user-guided boundary detection technique of this preferred embodiment, a more accurate boundary 640 can be formed, as shown in FIG. 6B.

Because a maximum velocity waveform can only have, by definition, a single value for each point in time, a profile line can be made one dimensional. That is, each spectrum can be analyzed separately to determine the maximum velocity waveform. Using two-dimensional profile lines may lead to a more accurate detected boundary, however, it is more computationally intensive because of the additional data that must be examined.

With any type of ultrasound image, the user-guided boundary detection technique described above offers a fast and easy alternative to manual tracing of a boundary when, for example, automatic boundary detection techniques generate erroneous boundaries or when a boundary is not automatically generated. Because the user-drawn boundary (i.e., the plurality of user-proposed transition positions) merely assists the detector in generating the boundary, the user does not need to precisely or carefully draw the boundary around the object of interest as he would in a purely manual boundary detection technique. This results in boundary generation that is much faster and less taxing on the user. Because this technique increases the rate at which the boundary is generated, calculations depending on the generated boundary can be performed more quickly. The user-guided boundary technique is made even easier to use when the ultrasound image is formed from a second harmonic frequency.

While any frequency band (such as a fundamental frequency band or a harmonic frequency band) can be used to generate the ultrasound image, it is preferred that second harmonic frequencies be used to generate the ultrasound image. Second harmonic frequencies produce ultrasound images with dramatically reduced acoustic clutter and better beamforming than the fundamental image counterpart, even under hard body conditions. As a result, the user-guided boundary detector 390 can more quickly and accurately identify actual-transition positions along profiles lines. Additionally, because the user will be able to visually identify the displayed boundary more easily, less time is required to trace the border. Conversely, ultrasound images with obscured borders make it more difficult for both the user and the detector to generate boundaries.

The imaging techniques described in all of the preferred embodiments above can be used for both tissue and contrast agent harmonic imaging. In contrast agent harmonic imaging, any one of a number of well-known non-linear contrast agents, such as micro-spheres, is added to the target or subject in order to enhance the non-linear harmonic response of the tissue or fluid. The contrast agents radiate ultrasonic energy at a harmonic of an insonifying energy at a fundamental frequency. In tissue harmonic imaging, no additional non-linear contrast agent is added to the target, and only the native non-linear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In this case no additional non-linear contrast agent is introduced into the tissue at any time during the imaging session. Since the harmonic imaging techniques described above can be used for both tissue and contrast agent harmonic imaging, it should be understood that the introduction of an added non-linear contrast agent into the tissue being imaged is not implied in any of the claims unless such added non-linear contrast agent is expressly recited.

Additionally, the border detection techniques described in all of the preferred embodiments above can be modified to detect a surface of a three-dimensional volume.

It is intended that the foregoing detailed description be understood as an illustration of selected forms that the invention can take and not as a definition of the invention. It is only the following claims, including all equivalents, that are intended to define the scope of this invention.

A preferred method of implementing user-guided boundary detection is listed in the software code below, which can be executed on Matlab software. For real time operation in an ultrasound system, it is preferred that this code be implemented in C or another suitable language.

```
function boundary (image_file)
% boundary (image_file)
%
% This routine performs user assisted boundary detection on the input image
%
% Input :
%                       image_file = image file name
global R0_user R_user R0_comp R_comp R0_disp R_disp z Nimage unit_normal0 unit_normal beta0 beta loc0 loc
% load image
eval (['load ',image_file]);
load heartsection;
% variables
[Nimage,Nimage] = size(z);
FIG = figure(1);
clg; clf;
set(gca,'Box','on','Position',[0 0 1 1],'Units','normalized','Visible','off');
% z = peaks(Nimage);
% z = zeros(Nimage,Nimage);
x = [0:1/(Nimage-1):1]; y = (0:1/(Nimage-1):1];
fv = find(ones(Nimage,1)*(x-.5).^2+(y-.5).'.^2*ones(1,Nimage) <= .0625);
% z(fv) = .5*ones(size(fv));
% image(x-1/(Nimage-1)/2,y-1/(Nimage-1)/2,z*63+1);
imagesc(x-1/(Nimage-1)/2,y-1/(Nimage-1)/2,flipud(z));
axis([0 1 0 1]);
axis('xy');
colormap(gray);
hold on;
set (FIG, 'Units','normalized');
set(gca,'Visible','off','Drawmode','Fast','Units','normalized');
set(FIG,'WindowButtonDownFcn', ['boundary_detect_on(',num2str(FIG),')']);
set(FIG,'WindowButtonUpFcn', ['boundary_detect_off(',num2str(FIG),')']);
function boundary_detect_on(FIG)
% boundary_detect_on(FIG)
%
% This routine starts the image boundary detection algorithm
%
% Input :
%                       FIG = handle of current figure
global R0_user R_user R0_comp R_comp R0_disp R_disp
% get current cursor position
cp = get(FIG,'CurrentPoint');
% set initial user defined boundary coordinates
R0_user(1,1) = cp(1);
R0_user(1,2) = cp(2);
% set initial computer and display boundary coordinates
R0_comp = R0_user;
R0_disp = R0_user;
R_user = R0_user;
R_comp = R0_user;
R_disp = R0_user;
% run boundary detection routine while cursor is in motion
set(FIG,'WindowButtonMotionFcn',['boundary_detect(',num2str(FIG),')'])
function boundary_detect(FIG)
% boundary_detect(FIG)
%
% This routine detects image boundaries based upon user input
%
% Input :
%                       FIG = handle of current figure
global R0_user R_user R0_comp R_comp R0_disp R_disp z Nimage unit_normal0 unit_normal beta0 beta loc0 loc
% variables
alpha = .6; gamma = .6;
Nvector = 2*round(.1*Nimage)+1;
Nwidth = 2*round(.025*Nimage)+1;
line = [-(Nvector-1)/2:(Nvector-1)/2].'/Nimage;
width = [-(Nwidth-1)/2:(Nwidth-1)/2].'/Nimage;
% get current cursor position
cp = get(FIG,'CurrentPoint');
% update user defined boundary coordinates
R_user = [R_user;[cp(1) cp(2)]];
[Nuser,Ncol] = size(R_user);
% compute boundary normal
if Nuser > 1
        % compute unit normal and unit normal data
        dx = R_user(Nuser,1)-R_user(Nuser-1,1);
        dy = R_user(Nuser,2)-R_user(Nuser-1,2);
        unit_vector = [dx dy]/norm([dx dy]);
        unit_normal = [-dy dx]/norm([dx dy]);
        if Nuser == 2
```

```
                unit_normal0 = unit_normal;
        else
                unit_normal = alpha*unit_normal0+(1-alpha)*unit_normal;
                unit_normal = unit_normal/norm(unit_normal);
                unit_normal0 = unit_normal;
        end
        vector0 = line*unit_normal+ones(Nvector,1)*R_user (Nuser,:);
        vector = vector0([1:Nvector].'*Ones(1,Nwidth),:)+width(Ones(Nvector,1)*[1:Nwidth])*unit_vector;
        zi = get_vector_data([0:Nimage-1]/Nimage,[0:Nimage-1]/Nimage,z,vector);
        zi = mean(reshape(zi,Nvector,Nwidth).').';
        % edge detect
        zi = conv(zi,hamming(11)/sum(hamming(11)));
        a = length(zi);
        zi = zi((11+1)/2:a-(11+1)/2+1);
        edge = abs(cumsum(zi-mean(zi)));
        [peak,loc] = max(edge);
        % location figure of merit
        if Nuser == 2
                loc0 = loc;
        else
                loc = round(gamma*loc0+(1-gamm)*loc);
                loc0 = loc;
        end
        % edge figure of merit
        fv = find(diff(sign(diff(edge))) ~= 0);
        beta = 1/length(fv);
        if Nuser == 2
                beta0 = beta;
        else
                beta = gamma*beta0+(1-gamma)*beta;
                beta0 = beta;
        end
        % update computer estimate
        R_comp = [R_comp;vector(loc,:)];
        [Ncomp,Ncol] = size(R_comp);
        % compute boundary display estimate
        R_disp = [R_disp;(1-beta)*R_user(Nuser,:)+beta*R_comp(Ncomp,:)];
        [Ndisp,Ncol] = size(R_disp);
        % plot boundary curve
        if Ncomp > 1
%                   [R_comp(Ncomp,1) R_comp(Ncomp-1,1)], . . .
%                   [R_comp(Ncomp,2) R_comp(Ncomp-1,2)],'m-', . . .
%                   [R_user(Nuser,1) R_user(Nuser-1,1)], . . .
%                   [R_user(Nuser,2) R_user(Nuser-1,2)], 'c-', . . .
                plot( . . .
                    [R_disp(Ndisp,1) R_disp(Ndisp-1,1)], . . .
                    [R_disp(Ndisp,2) R_disp(Ndisp-1,2)], 'g-', . . .
                    [vector0(1,1) vector0(Nvector,1)],[vector0(1,2) vector0(Nvector,2)],'g-', . . .
                    'EraseMode','none');                        % remove the (vector0 . . . to get rid of normal lines
                drawnow;
        end
%       figure(3)
%       plot line,5*(zi-mean(zi))/max(abs(zi-mean(zi))),line,edge/max(edge)*5,'c-','EraseMode','none');
%       axis([min(line) max(line) -10 10]);
%       grid;
%       drawnow;
%       figure(1)
end
function boundary_detect_off(FIG)
% boundary_detect_off (FIG)
%
% This routine terminates the image boundary detection algorithm
%
% Input :
%                   FIG = handle of current figure
global R0_user R_user R0_comp R_comp R0_disp R_disp
% terminate update of mouse position
set(FIG,'WindowButtonMotionFcn',' ');
% append initial user cursor position to user boundary
R_user = [R_user;R0_user];
[Nuser,Ncol] = size(R_user);
% append initial computer cursor position to computer boundary
R_comp = [R_comp;R0_comp];
[Ncomp,Ncol] = size(R_comp);
% append initial display cursor position to display boundary
R_disp = [R_disp;R0_disp];
[Ndisp,Ncol] = size(R_disp);
% connect initial and final boundary points
plot([R_user(Nuser-1,1) R_user(Nuser,1)],[R_user(Nuser-1,2) R_user(Nuser,2)],'c-', . . .
```

-continued

```
        [R_comp(Ncomp-1,1) R_comp(Ncomp,1)],[R_comp(Ncomp-1,2) R_comp(Ncomp,2)],'m-', . . .
        [R_disp(Ndisp-1,1) R_disp(Ndisp,1)],[R_disp(Ndisp-1,2) R_disp(Ndisp,2)],'g-', . . .
        'EraseMode','none');
drawnow;
% display boundary from user and computer
figure(2)
plot(R_user(:,1),R_user(:,2),'c-',R_comp(:,1),R_comp(:,2),'m-',R_disp(:,1),R_disp(:,2),'g-');
axis([0 1 0 1]);
grid;
legend('-','display','—','user input','-.','edge detection');
function zi = get_vector_data(x,y,z,vi)
% zi = get_vector_data(x,y,z,vi)
%
% This routine interpolates into z to get values along the vector vi = (xi,yi)
%
% Input :
%                x = x-axis [1 x Nx]       |   [Nx x 1]
%                y = y-axis [1 x Ny]       |   [Ny x 1]
%                z = matrix [Ny x Nx]
%                vi = vector (xi,yi)           [Nv x 2]
%
% Output :
%                zi = vector [Nv x 1]
% variables
Nx = length(x); Ny = length(y);
ax = (Nx-1)/(x(Nx)-x(1)); ay = (Ny-1)/(y(Ny)-y(1));
% computation section
index_x = ax*(vi(:,1)-x(1))+1;
index_y = ay*(vi(:,2)-y(1))+1;
nx = floor(index_x);
ny = floor(index_y);
nx = max(1,min(Nx-1,nx));            % clamp to x-axis limits
ny = max(1,min(Ny-1,ny));            % clamp to y-axis limits
index1 = ny+(nx-1)*Ny;
index2 = ny+nx*Ny;
index3 = ny+1+(nx-1)*Ny;
index4 = ny+1+nx*Ny;
alpha_x = index_x-nx;
alpha_y = index_y-ny;
% bilinear interpolation
zi = (1-alpha_y).*((1-alpha_x).*z(index1)+alpha_x.*z(index2))+ . . .
     alpha_y.*((1-alpha_x).*z(index3)+alpha_x.*z(index4));
```

What is claimed is:

1. A method for automatic boundary detection of an object of interest in an ultrasound image generated with harmonic imaging comprising the steps of:

(a) acquiring an ultrasound image from a subject using received ultrasonic energy at a harmonic of a fundamental frequency; and then (b) automatically generating a boundary oriented with respect to an object of interest in the ultrasound image.

2. The method of claim 1, wherein step (a) comprises the steps of:

(a1) transmitting ultrasonic energy at a fundamental frequency along a plurality of transmit lines; and (a2) receiving ultrasonic energy at a harmonic of the fundamental frequency along a plurality of receive lines, wherein a plurality of said receive lines are formed in response to one of said transmit lines.

3. The method of claim 2, wherein step (a2) comprises the step of receiving ultrasonic energy at a second order harmonic of the fundamental frequency.

4. The method of claim 1, wherein the subject is free of non-native non-linear contrast agents throughout an entire imaging session.

5. The method of claim 1 further comprising the step of providing a non-linear contrast agent in the subject during an imaging session.

6. The method of claim 1, wherein the ultrasound image comprises multiple spatial locations each associated with ultrasound image data, and wherein step (b) comprises the step of applying a threshold cut-off to the ultrasound image data of a plurality of spatial locations to detect a boundary.

7. The method of claim 1, wherein the ultrasound image comprises multiple spatial locations each associated with ultrasound image data, and wherein step (b) comprises the step of determining where a majority of ultrasound image data for both a current scan line and at least one previous scan line indicate similar reflections.

8. The method of claim 1, wherein step (b) comprises the step of analyzing gain levels in return pulses along at least one scan line in the ultrasound image.

9. The method of claim 1, wherein the ultrasound image comprises multiple spatial locations each associated with ultrasound image data, and wherein step (b) comprises the step of analyzing ultrasound value changes over succeeding display frames.

10. The method of claim 1, wherein step (b) comprises the step of analyzing ultrasound image data along radial lines emanating from a center of an object of interest in the ultrasound image.

11. The method of claim 1 further comprising the step of generating a user-guided detected boundary oriented with respect to the object of interest in the ultrasound image.

12. In an ultrasound system comprising a transducer, a receive beamformer responsive to the transducer, and a transmit beamformer coupled to the transducer, the improvement comprising:

means for acquiring an ultrasound image from a subject using harmonic information; and means for automatically generating a boundary oriented with respect to an object of interest in the ultrasound image; said means for acquiring and means for automatically generating being responsive to the receive beamformer.

13. The invention of claim 12, wherein said means for acquiring comprises:

means for transmitting ultrasonic energy at a fundamental frequency along a plurality of transmit lines; and means for receiving ultrasonic energy at a harmonic of the fundamental frequency along a plurality of receive lines, wherein a plurality of said receive lines are formed in response to one of said transmit lines.

14. The invention of claim 13, wherein said means for receiving ultrasonic energy at a harmonic of the fundamental frequency comprises means for receiving ultrasonic energy at a second order harmonic of the fundamental frequency.

15. The invention of claim 12, wherein said means for automatically generating comprises:

means for retrieving ultrasound image data associated with spatial locations in the ultrasound image; and means for processing ultrasound image data of a plurality of spatial locations to detect a boundary; said means for retrieving and means for processing being responsive to the receive beamformer.

16. The invention of claim 15, wherein means for processing ultrasound image data comprises means for applying a threshold cut-off to ultrasound image data of a plurality of spatial locations to detect a boundary.

17. The invention of claim 12, wherein the subject is free of non-native non-linear contrast agents throughout an entire imaging session.

18. The invention of claim 12 wherein the subject is provided with a non-linear contrast agent in the subject during an imaging session.

19. A method for user-guided detection of a boundary of an object of interest in an ultrasound image comprising the steps of:

(a) receiving a plurality of user-proposed transition positions oriented with respect to an object of interest in an ultrasound image; and (b) automatically generating a computed boundary oriented with respect to the object of interest, wherein the computed boundary is oriented at least partially as a function of at least one user-proposed transition position.

20. The method of claim 19, wherein step (b) comprises the steps of:

(b1) automatically selecting an actual transition position near a user-proposed transition position, said step of automatically selecting being repeated for a plurality of said plurality of user-proposed transition positions; and (b2) automatically generating a computed boundary oriented with respect to the object of interest, said computed boundary being oriented at least partially as a function of the actual transition positions automatically selected in step (b1).

21. A method for user-guided detection of a boundary of an object of interest in an ultrasound image comprising the steps of:

(a) receiving a plurality of user-proposed transition positions oriented with respect to an object of interest in an ultrasound image;

(b) automatically generating a set of actual-transition-position candidates along at least one profile line passing close to or through a user-proposed transition position, said step of automatically generating being repeated for a plurality of user-proposed transition positions;

(c) automatically selecting one actual transition position from the set of actual-transition-position candidates along said at least one profile line, the automatically selecting being made at least partially as a function of at least one user-proposed transition position of the plurality of user-proposed transition positions, said step of automatically selecting being repeated for a plurality of user-proposed transition positions; and (d) generating a computed boundary oriented with respect to the object of interest, said boundary being oriented at least partially as a function of the actual transition positions automatically selected in step (c).

22. The method of claim 21, wherein said at least one profile line in step (b) comprises a line normal to a tangent to a curve fitting the plurality of user-proposed transition positions.

23. The method of claim 21 further comprising the step of applying a filter to said at least one profile line before automatically generating the set of actual-transition-position candidates in step (b).

24. The method of claim 21, wherein said at least one profile line comprises ultrasound image data and wherein the set of actual-transition-position candidates is automatically generated in step (b) by applying a threshold cut-off to the ultrasound image data along said at least one profile line.

25. The method of claim 21, wherein said at least one profile line comprises ultrasound image data and wherein the set of actual-transition-position candidates is automatically generated along said at least one profile line in step (b) by calculating where a derivative of said at least one profile line is a maximum.

26. The method of claim 21, wherein said at least one profile line comprises ultrasound image data and wherein the set of actual-transition-position candidates is automatically generated along said at least one profile line in step (b) by calculating where an absolute value of an integral of said at least one profile line reaches a maximum.

27. The method of claim 21, wherein said at least one profile line comprises ultrasound image data and wherein the set of actual-transition-position candidates is automatically generated along said at least one profile line in step (b) by determining a location along said at least one profile line having a highest pixel intensity value.

28. The method of claim 21, wherein the automatically selecting of step (c) comprises the step of determining which actual-transition-position candidate is closest to the user-proposed transition position along a profile line.

29. The method of claim 21, wherein the automatically selecting in step (c) comprises the step of determining which actual-transition-position candidates is closest to a curve fitting the plurality of user-proposed transition positions.

30. The method of claim 21, wherein the automatically selecting in step (c) is made at least partially as a function of at least one previously automatically selected actual transition position.

31. The method of claim 21, wherein the automatically selecting in step (c) comprises the step of determining which actual-transition-position candidates is closest to a curve fitting a plurality of previously automatically selected actual transition positions.

32. The method of claim 21, wherein the computed boundary of step (d) comprises a curve fitting a plurality of actual transition positions.

33. The method of claim 21, wherein the computed boundary of step (d) is oriented additionally at least partially as a function of at least one user-proposed transition position.

34. The method of claim 21, wherein the generated boundary of step (d) is a curve fitting a plurality of computed positions, wherein a computed position comprises a weighed average of an actual transition position and a user-proposed transition position.

35. The method of claim 21, wherein the generated boundary of step (d) is a curve fitting a plurality of computed positions, wherein a computed position comprises an average of a plurality of actual transition positions along a plurality of profile lines.

36. The method of claim 21, wherein a user-selected transition position along a profile line is designated as an actual transition position in response to the non-existence of at least one actual-transition-position candidates along said profile line.

37. The method of claim 21, wherein a user-selected transition position is designated as an actual transition position in response to the actual transition position automatically selected in step (c) generating an erroneous boundary in step (d).

38. The method of claim 19 or 21, wherein the ultrasound image is (generated with received ultrasonic energy at a fundamental frequency.

39. The method of claim 19 or 21, wherein the ultrasound image is generated with received ultrasonic energy at a harmonic of the fundamental frequency.

40. The method of claim 19 or 21, wherein the ultrasound image is generated with received ultrasonic energy at a second order harmonic of the fundamental frequency.

41. The method of claim 19 or 21, wherein the ultrasound image is generated from a subject free of non-native non-linear contrast agents throughout an entire imaging session.

42. The method of claim 19 or 21, wherein the ultrasound image is generated from a subject and wherein the method further comprises the step of providing a non-linear contrast agent in the subject during an imaging session.

43. The method of claim 19 or 21, wherein the ultrasound image comprises a scan-converted ultrasound image and wherein the computed boundary comprises a boundary of an object of interest in the scan-converted ultrasound image.

44. The method of claim 19 or 21, wherein the ultrasound image comprises a spectral Doppler strip and wherein the computed boundary comprises an envelope of a maximum velocity waveform of the spectral Doppler strip.

45. In an ultrasonic imaging system comprising a transducer, a receive beamformer, and a transmit beamformer, the improvement comprising:

a interface means for receiving a plurality of user-proposed transition positions oriented with respect to an object of interest in an ultrasound image; and a user-guided boundary detection means for automatically generating a computed boundary oriented with respect to the object of interest at least partially as a function of at least one user-proposed transition position; said interface means and user-guided boundary detection means being responsive to the receive beamformer.

46. The invention of claim 45, wherein said user-guided boundary detection means comprises:

means for retrieving stored ultrasound image data along a plurality of profile lines; and means for determining an actual transition position from stored ultrasound image data along a plurality of profile lines.

47. The invention of claim 45, wherein said user-guided boundary detection means comprises:

means for automatically generating a set of actual-transition-position candidates along at least one profile line passing close to or through a user-proposed transition position;

means for automatically selecting one actual transition position from the set of actual-transition-position candidates along said at least one profile line at least partially as a function of at least one user-proposed transition position of a plurality of user-proposed transition positions; and means for generating a computed boundary oriented with respect to the object of interest at least partially as a function of automatically selected actual transition positions.

48. The invention of claim 45, further comprising:

means for transmitting ultrasonic energy to a subject at a fundamental frequency along a plurality of transmit lines; and means for receiving ultrasonic energy at a harmonic of the fundamental frequency along a plurality of receive lines, wherein a plurality of said receive lines are formed in response to one of said transmit lines.

49. The invention of claim 48, wherein said means for receiving ultrasonic energy at a harmonic of the fundamental frequency comprises means for receiving ultrasonic energy at a second order harmonic of the fundamental frequency.

50. The invention of claim 48, wherein the subject is free of non-native non-linear contrast agents throughout an entire imaging session.

51. The invention of claim 48, wherein the subject is provided with a non-linear contrast agent in the subject during an imaging session.

* * * * *

UNITED STATES PATENT AND TRADEMARK OFFICE
CERTIFICATE OF CORRECTION

PATENT NO. : 6,106,465
DATED : August 22, 2000
INVENTOR(S) : D. J. Napolitano et al.   Page 1 of 3

It is certified that error appears in the above-identified patent and that said Letters Patent is hereby corrected as shown below:

On the Title Page

On page 2, column 1, lines 5 and 6, under "OTHER PUBLICATIONS", delete "in in Vitro TIssue" and substitute --in In Vitro Tissue-- in its place.

In column 3, line 39, delete "10" and substitute --110-- in its place.

In column 4, line 46, delete "," (comma) immediately after "MHz".

In column 5, lines 12 and 13, delete "suimnmed" and substitute --summed-- in its place.

In column 6, line 49, delete "(gain" and substitute --gain-- in its place.

In column 8, line 40, delete "Clark" and substitute --dark-- in its place.

In column 11, line 19, delete "y = (0:1/" and substitute --y = [0:1/-- in its place.

UNITED STATES PATENT AND TRADEMARK OFFICE
CERTIFICATE OF CORRECTION

PATENT NO. : 6,106,465
DATED : August 22, 2000
INVENTOR(S) : D. J. Napolitano et al.

It is certified that error appears in the above-identified patent and that said Letters Patent is hereby corrected as shown below:

In column 13, line 4, delete "(unit_normal)," and substitute --(unit_normal);-- in its place.

In column 13, line 8, delete "Ones" (both occurrences) and substitute --ones-- in its place (both occurrences).

In column 13, line 21, delete "(1-gamm)" and substitute --(1-gamma)-- in its place.

In column 13, line 41, delete "% remove the (vector" and substitute --% remove the [vector-- in its place.

In column 13, line 44, delete "figure(3)" and substitute --figure(3);-- in its place.

In column 13, line 45, delete "plot" and substitute --plot)-- in its place.

In column 13, line 49, delete "figure(1)" and substitute --figure(1);-- in its place.

UNITED STATES PATENT AND TRADEMARK OFFICE
CERTIFICATE OF CORRECTION

PATENT NO. : 6,106,465
DATED : August 22, 2000
INVENTOR(S) : D. J. Napolitano et al.

It is certified that error appears in the above-identified patent and that said Letters Patent is hereby corrected as shown below:

In column 15, line 10, delete "'—'" and substitute --'--'-- in its place.

In claim 38, line 2, delete "(generated" and substitute --generated-- in its place.

Signed and Sealed this

Twenty-ninth Day of May, 2001

Attest:

NICHOLAS P. GODICI

Attesting Officer     *Acting Director of the United States Patent and Trademark Office*